(12) United States Patent
Bauer

(10) Patent No.: US 10,934,179 B2
(45) Date of Patent: Mar. 2, 2021

(54) LIQUID TREATMENT SYSTEM AND METHOD

(71) Applicant: EBED Holdings Inc., Baden (CA)

(72) Inventor: Walter Jacob Bauer, Baden (CA)

(73) Assignee: EBED Holdings Inc., Baden (CA)

( * ) Notice: Subject to any disclaimer, the term of this patent is extended or adjusted under 35 U.S.C. 154(b) by 522 days.

(21) Appl. No.: 15/568,735

(22) PCT Filed: Apr. 25, 2016

(86) PCT No.: PCT/CA2016/050479
§ 371 (c)(1),
(2) Date: Oct. 23, 2017

(87) PCT Pub. No.: WO2016/168943
PCT Pub. Date: Oct. 27, 2016

(65) Prior Publication Data
US 2018/0134583 A1 May 17, 2018

Related U.S. Application Data

(60) Provisional application No. 62/194,567, filed on Jul. 20, 2015, provisional application No. 62/152,648, filed on Apr. 24, 2015.

(51) Int. Cl.
*C02F 1/32* (2006.01)
*A23L 3/358* (2006.01)
(Continued)

(52) U.S. Cl.
CPC ............. *C02F 1/325* (2013.01); *A01N 59/00* (2013.01); *A23L 3/28* (2013.01); *A23L 3/358* (2013.01);
(Continued)

(58) Field of Classification Search
CPC ...... C02F 1/325; C02F 1/763; C02F 2303/04; C02F 1/32; A61L 2/10; A61L 2/18;
(Continued)

(56) References Cited

U.S. PATENT DOCUMENTS 4,609,471 A * 9/1986 Beemster ................ C02F 1/325
210/748.06
5,753,106 A 5/1998 Schenck
(Continued)

FOREIGN PATENT DOCUMENTS

| CA | 2888661 A1 | 4/2015 |
|---|---|---|
| CN | 102910772 A | 2/2013 |

(Continued)

OTHER PUBLICATIONS

International Search Report and Written Opinion of the ISA/CA dated Jul. 6, 2016 in International Application No. PCT/CA2016/050479; 10pgs.
(Continued)

*Primary Examiner* — Cameron J Allen
(74) *Attorney, Agent, or Firm* — Haukaas Fortius PLLC; Michael H. Haukaas

(57) ABSTRACT

A method of treating a liquid, the method including: receiving a chemically treated liquid; passing the chemically treated liquid through a nanobubble generator to produce a nanobubble-containing liquid; treating the nanobubble-containing liquid with disinfecting radiation to produce a resultant liquid; and releasing the resultant liquid for use. A liquid treatment system including: a source of liquid; a chemical treatment station to test the chemical content of the source liquid and, if necessary, provide an appropriate amount of chemical treatment to the liquid to provide a chemically treated liquid; a nanobubble generator in fluid communication with the chemical treatment station that generates (Continued)

nanobubbles to provide a nanobubble liquid; a radiation-based disinfecting unit (RDU) in fluid communication with the nanobubble generator that exposes the nanobubble liquid to radiation and provides treated liquid; a pump to produce a liquid flow through the system; and an outlet through which the treated liquid flows.

18 Claims, 6 Drawing Sheets

(51) Int. Cl.
| | |
|---|---|
| *A23L 3/28* | (2006.01) |
| *A01N 59/00* | (2006.01) |
| *A61L 2/18* | (2006.01) |
| *A61L 2/28* | (2006.01) |
| C02F 9/00 | (2006.01) |
| *A61L 2/16* | (2006.01) |
| *A61L 2/10* | (2006.01) |
| *C02F 1/30* | (2006.01) |
| *C02F 1/76* | (2006.01) |
| *C02F 101/00* | (2006.01) |
| *C02F 1/48* | (2006.01) |
| *C02F 101/32* | (2006.01) |
| *C02F 1/44* | (2006.01) |
| *A61L 2/02* | (2006.01) |
| *C02F 101/10* | (2006.01) |
| *C02F 1/40* | (2006.01) |
| *C02F 1/28* | (2006.01) |
| *C02F 101/20* | (2006.01) |
| *C02F 1/00* | (2006.01) |
| *C02F 1/34* | (2006.01) |
| *C02F 1/64* | (2006.01) |
| *C02F 1/42* | (2006.01) |

(52) U.S. Cl.
CPC .................. *A61L 2/10* (2013.01); *A61L 2/16* (2013.01); *A61L 2/18* (2013.01); *A61L 2/183* (2013.01); *A61L 2/28* (2013.01); *C02F 9/00* (2013.01); *A23V 2002/00* (2013.01); *A61L 2/022* (2013.01); *A61L 2202/11* (2013.01); *A61L 2202/14* (2013.01); *C02F 1/001* (2013.01); *C02F 1/283* (2013.01); *C02F 1/30* (2013.01); *C02F 1/32* (2013.01); *C02F 1/34* (2013.01); *C02F 1/40* (2013.01); *C02F 1/42* (2013.01); *C02F 1/442* (2013.01); *C02F 1/444* (2013.01); *C02F 1/48* (2013.01); *C02F 1/64* (2013.01); *C02F 1/76* (2013.01); *C02F 1/763* (2013.01); *C02F 2101/006* (2013.01); *C02F 2101/101* (2013.01); *C02F 2101/103* (2013.01); *C02F 2101/105* (2013.01); *C02F 2101/206* (2013.01); *C02F 2101/32* (2013.01); *C02F 2209/006* (2013.01); *C02F 2303/04* (2013.01); *C02F 2303/26* (2013.01); *Y02W 10/37* (2015.05)

(58) Field of Classification Search
CPC ........ A61L 2202/14; A23L 3/28; A23L 3/358; A23V 2002/00
See application file for complete search history.

(56) References Cited

U.S. PATENT DOCUMENTS

| | | | |
|---|---|---|---|
| 5,785,845 | A | 7/1998 | Colaiano |
| 2011/0000860 | A1 | 1/2011 | Bland et al. |
| 2011/0024361 | A1 | 2/2011 | Schwartzel et al. |
| 2012/0031852 | A1 | 2/2012 | Aglietto |
| 2016/0236158 | A1* | 8/2016 | Bauer .................. B01F 5/0608 |

FOREIGN PATENT DOCUMENTS

| | | | |
|---|---|---|---|
| CN | 203 482 710 | | 3/2014 |
| CN | 104925896 A | * | 9/2015 |
| JP | 2009255011 A | * | 11/2009 |
| RU | 113266 U1 | | 2/2012 |
| RU | 2013145613 A | | 4/2015 |
| WO | 2009123749 A2 | | 10/2009 |

OTHER PUBLICATIONS

Extended European Search Report on corresponding EP patent application No. 16782440.8, dated Nov. 19, 2018.
Federal Institute of Industrial Property (FIIP), Office Action received on corresponding Russian patent application No. 2017140215, Oct. 14, 2019.
European Patent Office, Office Action received on corresponding European patent application No. 16 782 440.8, dated Dec. 17, 2019.
Espacenet, English translation of Abstract of CN 102910772, retrieved on Jan. 13, 2020.
Espacenet, English translation of Abstract of RU 2013145613, retrieved on Jan. 13, 2020.
Espacenet, English translation of Abstract of RU 113266, retrieved on Jan. 13, 2020.

* cited by examiner

LIQUID TREATMENT SYSTEM AND METHOD

RELATED APPLICATIONS

This application is a National Stage filing under 35 U.S.C. § 371 of International Application No. PCT/CA2016/050479 filed Apr. 25, 2016, which claims priority under 35 U.S.C. § 119(e) to U.S. Provisional Patent Application Nos. 62/152,648 filed Apr. 24, 2015 and 62/194,567 filed Jul. 20, 2015, which applications are incorporated herein by reference.

FIELD

The present disclosure relates to a system and a method of treating liquid solutions. In particular, the present disclosure relates to a system and a method for treating a liquid containing a chemical treatment with a radiation-based disinfecting unit.

BACKGROUND

Waterborne diseases are often caused by pathogenic microorganisms that are transmitted in contaminated water. Infection can result during bathing, washing, drinking, in the preparation of food, or the consumption of food thus infected. Various forms of waterborne diarrheal disease are probably the most prominent examples. According to the World Health Organization, such diseases account for an estimated 4.1% of the total daily global burden of disease, and cause about 1.8 million human deaths annually. The World Health Organization estimates that 88% of that burden is attributable to unsafe water supply, sanitation and hygiene. Even in developed nations, there have been issues with bacteria in water systems that have caused significant harm to populations. As such, there is a need therefore for improved water treatment systems, methods and apparatuses. If such systems, methods and apparatuses can be provided at a lower cost and smaller footprint, they could also address the constraints and requirements of poor, rural, mountainous, and/or densely populated communities.

In addition to water, there are other liquids that may also benefit from improved sterilization/cleaning such as those in the food and beverage industry. For example, chemicals, such as chlorine compounds, ozone and the like, are widely used in the food and beverage industry to reduce bacteria and disinfect or sanitize liquids. Examples include treating pasteurizer cooling water, washing fruit and vegetables and disinfecting food contact surfaces. Chlorine compounds are also commonly used to disinfect water or other liquids in containers.

Among the chlorine compounds, chlorine dioxide (ClO2) is a potent oxidizing agent used in water treatment and in bleaching. As a disinfectant ClO2 has stronger biocidal capacity than that of chlorine.

Two mechanisms are usually used to generate chlorine dioxide: by reacting sodium chlorite with chlorine gas or hydrochloric acid (two chemical compounds system) or by reacting sodium chlorite with sodium hypochlorite and an acid like hydrochloric acid or sulphuric acid (three chemical compounds system).

2NaClO2+Cl2→2ClO2+2NaCl (two compounds)

5NaClO2+4HCl→4ClO2+5 NaCl+2H2O (two compounds)

2NaClO2+NaOCl+H2SO4→2ClO2+NaCl+Na2SO4+H2O (three compounds).

2NaClO2+NaOCl+2HCl→2ClO2+3NaCl+H2O (three compounds).

The sanitation of wastewater with chlorine dioxide is caused by oxidation. The chlorine dioxide undergoes oxidation to affect the reproduction and metabolism of microorganisms. Chlorine dioxide is generally considered to have over two and a half times the oxidation power of chlorine. Chlorine dioxide's oxidation reduction potential (0.95V) is much lower than chlorine (1.36V) but its oxidation capacity (5) is much greater than chlorine (2). The oxidation reduction potential (ORP) measures an oxidizer's strength or speed at which it reacts with an oxidizable material. Although chlorine dioxide has a low ORP, it is more selective as to the types of oxidizable materials with which it reacts. Chlorine dioxide targets specific organic molecules including cysteine, tyrosine, methoionyl, DNA and RNA. By comparison, chlorine and ozone have much broader reactions. The oxidation capacity indicates that on a molar basis chlorine dioxide has a greater capacity for disinfecting over chlorine. The selectivity and oxidation capacity of chlorine dioxide makes it a stronger oxidative disinfectant than chlorine ("Evaluation of a Chlorine Dioxide Secondary Disinfection System," Frank P. Sidari III and Jeanne VanBriesen, Ph.D. Water & Wastes Digest, Thu, 2002-10-24 13:39).

Chlorine dioxide will cause suspended particles in solution to attract each other, allowing them to be easily filtered. Because of this, "cloudy" water is readily cleaned by chlorine dioxide along with a filter.

Chlorine dioxide is effective against a variety of pathogens, but it has limitations. Mold and yeast spores are reduced 80 to 99% by chlorine dioxide concentrations of 0.75 to 5 ppm (parts per million) in water. Bacteria and viruses are also greatly reduced with the use of chlorine dioxide.

Chlorine dioxide's effectiveness may be reduced by iron and manganese content. Iron may be present in water at many produce operations. Accordingly, liquids containing either of these two metals may preferably be filtered before disinfection.

Chlorine dioxide gas in concentrated amounts (greater than 30% volume in air) is spontaneously explosive. Chlorine dioxide should not be stored or transported because it is unstable at normal conditions and explosive under pressure. Accordingly, it is necessary to make some provision for diluting the gases produced in the reaction. Air and hydrogen have commonly been used as the diluent gases. Chlorine dioxide may be dissolved in water in a concentration of, for example, up to about 10 grams per liter.

Various factors may affect the sanitizing power of chlorine compounds. These factors include the presence of organic material, pH, temperature, concentration, contact time, and the like.

In some situations, chemical treatments may be added to or used with liquids to alter characteristics of the liquid other than for disinfection, for example, to add color or the like.

Ultraviolet (UV) light is also used in some applications to sterilize and treat liquids such as water, wastewater and others. Short-wavelength ultraviolet radiation (UV-C) is understood to attack the DNA of pathogenic and other microorganisms directly. The microorganisms, such as bacteria, lose their reproductive capability and are destroyed. Studies have shown that even parasites such as *cryptosporidia* or *giardia*, which are extremely resistant to chemical disinfectants, are efficiently reduced with UV light exposure. A combination of UV light and chemical treatments to treat liquids would appear to be useful. However, many types of chemical treatments, including treatment with chlorine-based disinfectants, such as $NH_2Cl$, $HOCl$, and $OCl(—)$ and $ClO_2$, photodegrade under UV irradiation, reducing their effectiveness. Further, if UV light is also used at higher doses in some applications, it can act to remove the chemical treatment, such as chlorine and chloramine species, in a process called photolysis, which could offset the impact of the chemical treatment, such as chlorination of the water. As such, this combination has generally not been used.

There remains a need for improved systems and methods of treating liquids and, in particular, systems and methods to produce liquids containing chemical treatments that are more stable, does not off gas, even at high concentrations, and that have higher oxidation-reduction potential.

SUMMARY

According to one aspect herein, there is provided a liquid treatment system including: a source of liquid; a chemical treatment station to test the chemical content of the source liquid and, if necessary, provide an appropriate amount of chemical treatment to the liquid to provide a chemically treated liquid; a nanobubble generator in fluid communication with the chemical treatment station that generates nanobubbles in the chemically treated liquid to provide a nanobubble liquid; a radiation-based disinfecting unit (RDU) in fluid communication with the nanobubble generator that exposes the nanobubble liquid to radiation and provides treated liquid; a pump to produce a liquid flow through the system; and an outlet through which the treated liquid flows.

In a particular case, the nanobubble generator may include: a housing having an inflow portion for receiving a source liquid, an outflow portion for releasing a nanobubble containing liquid, and a treatment portion disposed between the inflow and outflow portions for treating the source liquid, the treatment portion having at least two sequential shear surface planes separated by cavitation spaces, chambers or zones.

In another particular case, the RDU may include: an RDU inlet operatively connected to the nanobubble generator; a disinfecting unit in fluid communication with the RDU inlet including an enclosure and a radiation emitting means; and a RDU outlet for releasing a radiation-treated liquid from the disinfecting unit.

In the above cases, the testing the chemical content may include determining if the source liquid contains an appropriate amount of chemical for disinfecting the source liquid in conjunction with the nanobubble generator and the RDU. In a particular case, the chemical may include chlorine dioxide. In this case, the chlorine dioxide may be injected to provide between approximately 0.5 and 5 ppm at the nanobubble generator. More particularly, the chlorine dioxide may be injected to provide between approximately 3 and 4 ppm at the nanobubble generator.

In the above cases, the pump may be configured to produce a pressure at the nanobubble generator of between approximately 1 and approximately 10 bar. In some cases, the pressure may be between approximately 2 and approximately 5 bar.

Also, in the above cases, the radiation may be electromagnetic radiation and, in a particular case, ultra-violet radiation.

According to another aspect herein, there is provided a method of treating a liquid, wherein the method includes passing a source liquid through a liquid treatment system according to the above aspect.

According to yet another aspect herein, there is provided a method of treating a liquid, the method including: receiving a chemically treated liquid; passing the chemically treated liquid through a nanobubble generator to produce a nanobubble-containing liquid; treating the nanobubble-containing liquid with disinfecting radiation to produce a resultant liquid; and releasing the resultant liquid for use.

In a particular case, the chemically treated liquid may include a source liquid exposed to chemical treatment to produce the chemically treated liquid. In this case, the chemical treatment may include injecting a suitable amount of chemical into the source liquid. Further, the suitable amount may include an amount of chemical for disinfecting the source liquid in conjunction with the nanobubble generator and the disinfecting radiation.

In the above cases of the method, the flow of liquid may be driven at a pressure of between approximately 1 bar and approximately 10 bar at the nanobubble generator. More particularly, the pressure may be between approximately 2 and approximately 5 bar.

In the above cases of the method, the radiation may be electromagnetic radiation and, in a particular case, ultra-violet radiation. The ultra-violet radiation may be delivered at approximately 200 to 250 $mJ/cm^2$.

In any of the above aspects or cases, the source liquid may be water, including potable, wastewater and recycled water.

According to another aspect herein, there is provided a liquid treatment system as both generally and specifically described herein with reference to and as illustrated by the accompanying drawings.

According to still another aspect herein, there is provided a method of treating liquid as both generally and specifically described herein with reference to and as illustrated by the accompanying drawings.

According to yet another aspect, there is provided a liquid treatment system including a nanobubble generator in fluid communication with a radiation-based disinfecting unit (RDU). In particular, the RDU may include a disinfecting inlet operatively connected to the outflow portion of the nanobubble generator, a disinfecting enclosure housing a radiation emitting means, such as a UV lamp, and a disinfecting outlet for releasing treated liquid, the inflow portion, the treatment portion, the outlet portion, the disinfecting inlet, the disinfecting enclosure and the disinfecting outlet in fluid communication with each other.

According to yet another aspect, there is provided a method of treating a source liquid, the method includes: passing the source liquid through a nanobubble generator thereby producing a nanobubble-containing liquid; and treating the nanobubble-containing liquid with radiation, such as UV radiation. The source liquid may be a mixture of different liquids. Further, the source liquid may be a mixture of a liquid and a gas. In some cases, the gas is a combination of different gases. In other cases, the gas is a gas naturally occurring in the liquid or added to the liquid. In a particular case, the gas is added via an injection step.

In the above aspects and cases, the nanobubbles are preferably present in a relatively high concentration in the treated liquid and are in the nano-size range, preferably between about 10 and about 2000 nanometers, more preferably between about 10 nm and about 150 nm.

BRIEF DESCRIPTION OF THE DRAWINGS

The following figures illustrate various aspects and embodiments of the system, method and apparatus for liquid treatment disclosed herein.

DESCRIPTION

Figure 1:
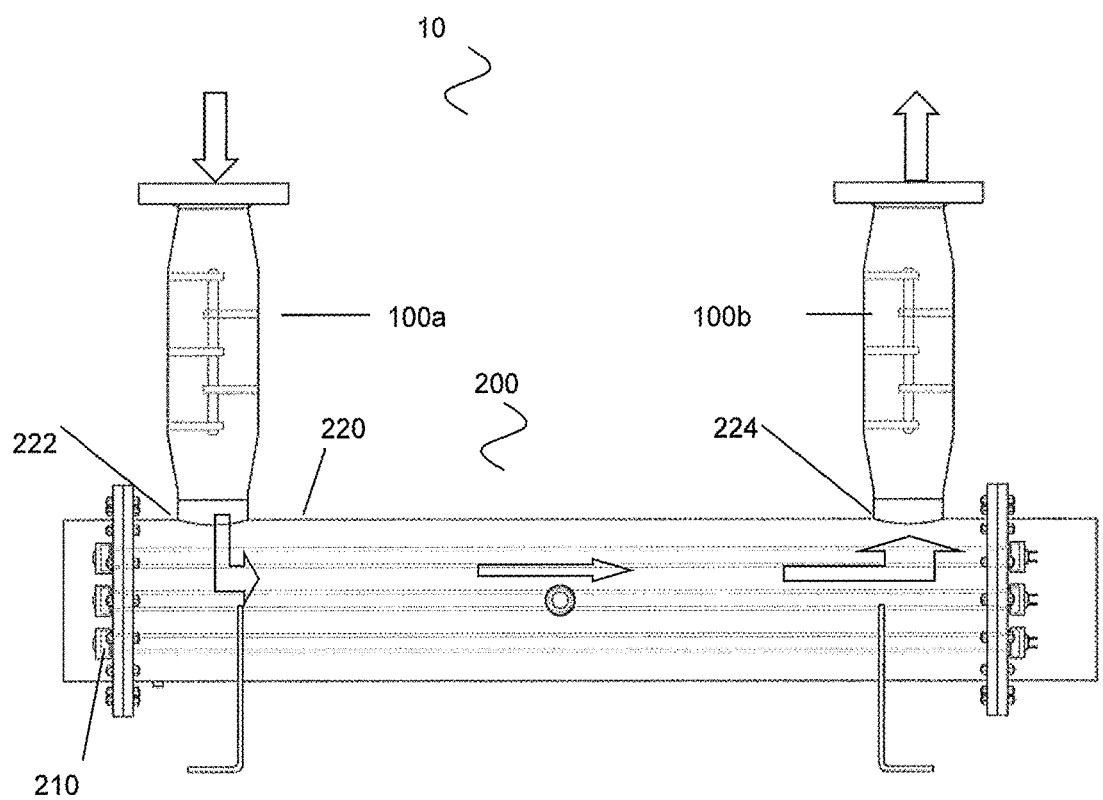
FIG. 1 illustrates a side view of a liquid treatment apparatus or system according to an embodiment.

Unless defined otherwise, all technical and scientific terms used herein have the same meaning as commonly understood by one of ordinary skill in the art. Also, unless indicated otherwise, except within the claims, the use of "or" includes "and" and vice versa. Non-limiting terms are not to be construed as limiting unless expressly stated or the context clearly indicates otherwise (for example "containing", "including", "having" and "comprising" typically indicate "including without limitation"). Examples of limiting terms include "consisting of" and "consisting essentially of". Singular forms including in the claims such as "a", "an" and "the" include the plural reference unless expressly stated otherwise.

In order to aid in the understanding and preparation of the within system, method and apparatus, the following illustrative, non-limiting, examples are provided.

Generally, the method, system and apparatus provided herein combine radiation-based disinfection, such as ultraviolet (UV) radiation, and chemical treatments, such as chlorine treatment. Embodiments of the method, system and apparatus herein allow the two treatment types to be used together and yield unexpected results.

Generally speaking, the system, method and apparatus include a source of liquid, a treatment module and an outlet for the treated liquid. The treatment module may include a chemical treatment section, a nanobubble generator, and a radiation-based disinfecting unit. The chemical treatment section adjusts levels of chemicals in the liquid to be appropriate for disinfection, the nanobubble generator creates nanobubbles in the liquid and the radiation-based disinfecting unit treats the liquid for disinfection.

It is intended that the method, system and apparatus disclosed herein will reduce or prevent the photodegradation of chemicals in the presence of radiation, thus allowing for each treatment type to be effective. The liquid treatment system is intended to be effective in a variety of applications as described herein.

The system, method and apparatus disclosed herein are also intended to combine the disinfecting power of ultra violet radiation with chemicals to disinfect a liquid without changing the elemental composition of the source liquid material. With the system and method for liquid treatment, disinfecting chemicals such as chlorine-based disinfectants (for example, sodium hypochlorite, chlorine dioxide, Hypochlorites, Chloramine), bromine-based disinfectants, peracetic acid $(C_2H_4O_3)$ (PAA), ozone and the like are intended to be protected from photodegradation under UV radiation.

The system, method and apparatus disclosed herein are intended to produce chemical disinfectant (such as chlorine dioxide $(ClO_2)$) containing liquids that are more stable, have reduced off gassing, have enhanced oxidation of manganese to provide more effective filtering of manganese, and between 50-100 mV higher ORP than conventional chemical disinfectant containing liquids. Although several specific embodiments are described, it will be apparent that the disclosure is not limited to the embodiments illustrated, and that additional embodiments may also be available. The nanobubble-containing $ClO_2$ solution of the present disclosure is intended to be effective in a variety of applications, some of which are described herein below.

The system, method and apparatus may be implemented in a stationary unit or in a portable unit. In some embodiments, the system, method and apparatus for liquid treatment may not require external air or gas to produce nanobubbles or to create a greater abundance of nanobubbles in a source liquid solution, and do not require a nanobubble or microbubble base or source liquid solution.

With reference to FIG. 1, an embodiment of a liquid treatment system 10 includes one or more nanobubble generators 100a, 100b and a radiation-based disinfecting unit (RDU) 200. The nanobubble generator 100a, 100b and the radiation-based disinfecting unit 200 are in fluid communication with one another. In this embodiment, a source liquid that already contains or has been injected with a chemical disinfectant flows in the direction of the block arrows: through a first nanobubble generator 100a, through the RDU for radiation, and through the second nanobubble generator 100b.

In the embodiment shown in FIG. 1, the system 10 includes two nanobubble generators. However, it should be understood that the systems may include any number of nanobubble generators, for example, the system may include three or more nanobubble generators. Likewise, the system may include two or more radiation-based disinfecting units. Systems with 3, 4, 5 or more nanobubble generators and with 2, 3, 4, 5 or more RDUs may be made without difficulty. A manifold may be used for multiple units.

If the system includes a single nanobubble generator, this nanobubble generator will be located between the source of the chemical treatment-containing liquid and the RDU, such that nanobubble containing liquid reaches the RDU.

Nanobubble Generator

With reference to FIGS. 2-5, an example nanobubble generator 100 includes a housing 110 having an inflow portion 140 for receiving the source liquid solution, an out-flow portion 150 for releasing the nanobubble-containing liquid solution, and a treatment portion 115 between the inflow 140 and outflow 150 for treating the source liquid solution. It will be understood that other types of nanobubble generators may be available or developed in the future and the example nanobubble generator 100 is for illustrative purposes. Further description of a nanobubble generator may be found in International Application No. PCT/CA2014/050957 (Publication No. WO2015/048904) of Walter Bauer.

Figure 2:
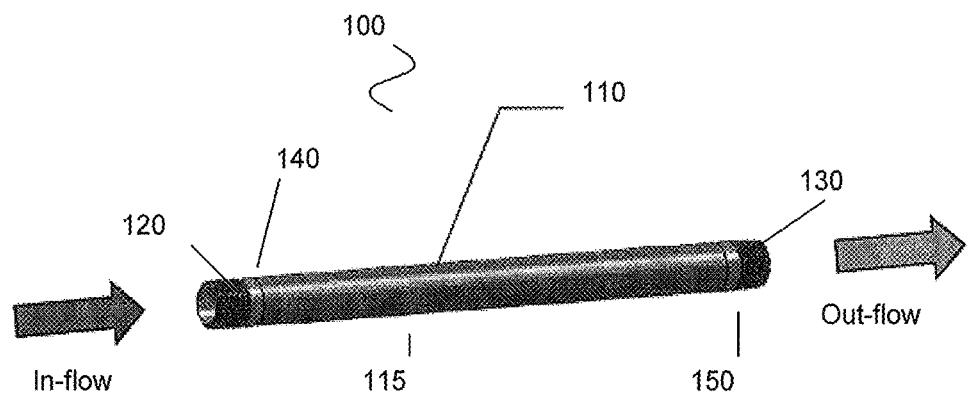
FIG. 2 illustrates a perspective view of an example nanobubble generator for use in a system or method according to an embodiment.
Figure 3:
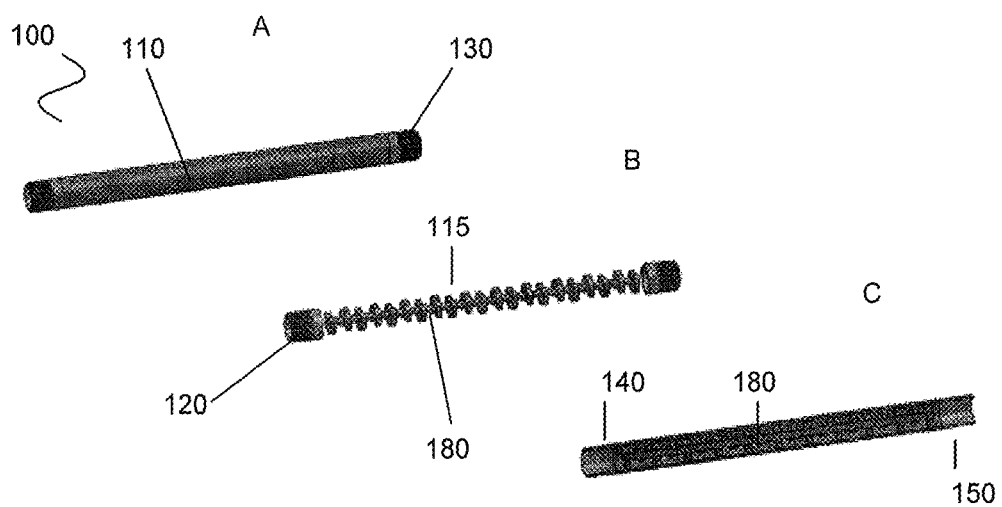
FIG. 3 illustrates an outer view (A), transparent view (B) and longitudinal cross sectional view (C) of the nanobubble generator of FIG. 2.

With reference to FIGS. 2 and 3A, in this embodiment, the housing 110 may take a substantially tubular form. The inlet 140 and outflow 150 portions may include a threaded boss 120 and 130 at each end. The housing 110 and bosses 120 and 130 are preferably made of a substantially inert material, such as polyvinyl chloride (PVC).

Figure 4:
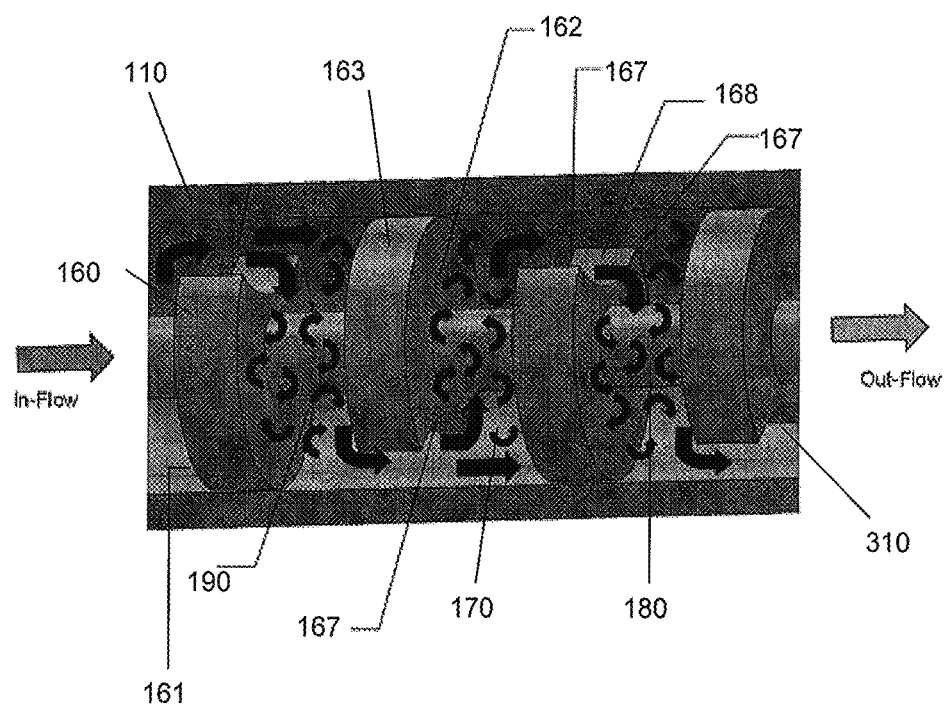
FIG. 4 illustrates an enlarged view of a longitudinal cross section of the nanobubble generator of FIG. 2.

With reference to FIGS. 3B and 3C and 4 the treatment portion 115 of the nanobubble generator may include a series of sequential cavitation zones 190 and shear surface planes 168. The series of sequential cavitation zones 190 and shear surface planes 168 may be enabled by having a generally elongated member 180 having a series (2 or more) of spaced apart elements 160 which extend axially through the housing 110 and are interposed between the inflow and the outflow portions of the nanobubble generator. In some embodiments, other numbers of spaced apart elements 160 may be provided, for example, 5 elements, 10 elements, 20 elements, 30 elements or the like depending on the application for the nanobubble generator. Further, more than 30 spaced apart elements 160 may also be used. Each element 160 may take the form of a disc. The disc-like elements 160 may be supported upon or mounted on a central rod or shaft 180. With reference to FIG. 4, the disc 160 may include opposite walls 161, 162 (also referred to as shear walls), and a peripheral or side wall 163. One shear wall 161 may face the inflow portion and the opposite shear wall 162 may face the outflow portion of the generator. The peripheral wall 163 may extend between opposite shear walls 161, 162. The disc-like elements 160 are held in spaced relation to each other and may be separated from one another by a space 170.

As illustrated in FIG. 4 each element 160 may be formed with at least one groove or notch 310 extending downwards from the peripheral wall 163. In some cases, each element 160 may include an aperture instead of a groove or notch. Each groove or notch 310 may include edges or shear edges 167 and a shear surface plane 168 between the shear edges 167. The shear surface plane 168 may be viewed as a continuation of the peripheral walls 163 into the grooves 310. The edges 167, which may have a scallop design, may be substantially sharp.

Figure 5:
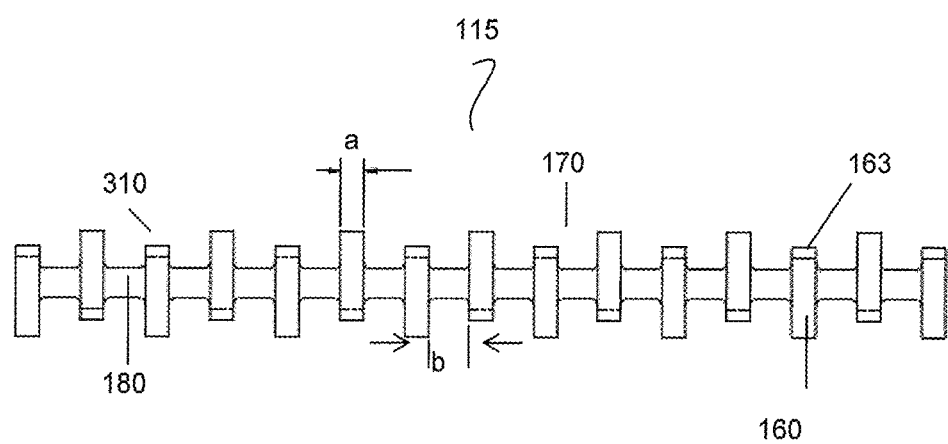
FIG. 5 illustrates a treatment portion of the nanobubble generator of FIG. 2.

In an embodiment as illustrated in FIG. 5, the width "a" of each disc-like element 160, and therefore the width of the shear plane surface, is about one half the distance "b" between two consecutive disc-like elements 160.

As illustrated in FIG. 5, the axially successive disc-elements 160 are arranged along the rod 180 with their notches or grooves circumferentially staggered in relation to one another. The elements 160 may be arranged on rod 180 such that the notches 310 in each element 160 are alternating. That is, in relation to FIG. 5, if a notch in one disc-like element is facing down, the notch in the following disc-like element would be facing up.

The disc-like elements may be manufactured from a single metal. Preferably the disc-like elements may be made of a corrosion resistant metal. Preferably, the disc-like elements may be made from stainless steel 300 series, such as 316L. It is believed that the nanobubble generator produces ions through the shearing action on water as the water passes over the elements/discs 160, which ions then act as catalysts in creating an endothermic reaction. Preferably the discs are laser cut.

As shown in FIG. 4 each disc-like element 160 may be disposed substantially perpendicular to the direction of flow of the liquid solution within the housing 110, such that the elements 160 may substantially block any direct fluid flow through the housing 110 and as a result the fluid flow passes through the notches, grooves or apertures 310 in each of the discs. Due to the alternating arrangement of the notches the fluid flow between the discs 160 is turbulent and by virtue of the differing cross-sectional areas of the apertures 310 in each disc 160, the width of the discs, and the space 170 between the discs 160 the fluid is caused to accelerate and decelerate on its passage through the housing 110 to ensure a turbulent flow over the surfaces of the discs 160. In some cases, the nanobubble generator may configured to be unidirectional and unipositional as shown by the arrows in FIGS. 1, 2 and 4.

The chemically treated liquid is passed through the nanobubble generator at a suitable pressure to produce nanobubbles. In some embodiments, the pressure may be between about 1 bar (100 kPa) and 10 bar (1 Mpa), although the maximum pressure may be more appropriately only limited by the structural integrity of the system. In some embodiments, the pressure may be between about 2 bar (200 kPa) and 5 bar (500 kPa), 3 bar (300 kPa) to 4 bar (400 kPa), or the like. In one particular embodiment, the suitable pressure may be about 3.2 bar (320 kPa).

Testing has shown that there is an endothermic reaction when water passes through the nanobubble generator, in which the water cools down, for example, from between 2 to 4 degrees Celsius, upon first treatment. This is indicative of an energy conversion within the water body itself. The reaction may be initiated by the energy of the water flow at pressure over the series of elements within the generator.

With reference to FIG. 4, as liquid (represented by the broad arrows in FIG. 4) enters into the cavitation zone or chamber 190, a number of reactions may be taking place substantially simultaneously, including: shear, cavitation, micro jet formation, streaming current/zeta potential formation, electrolysis, nanobubble formation, nucleation of crystals and a re-organization of the water liquid structure.

As liquid solution flows through the nanobubble generator the simultaneous reactions referred to above, may be replicated sequentially according to the formula n−1 times, wherein "n" is the number of disc-like elements 160 within the housing 110, to increase the kinetic energy frequency of the solution.

The resultant nanobubble containing liquid is intended to have increased paramagnetic qualities that may influence the properties of the liquid. For example, in water it may alter cleaning properties, steam and ice production, thermal transfer and even the energy needed to pump water. It may reduce scaling, biofilm and biofouling and may alter the way in which water interacts with oils and fats.

Radiation-Based Disinfecting Unit

Referring back to FIG. 1, the radiation-based disinfecting unit (RDU) 200 may be a sealed enclosure 220. The RDU 200 exposes the nanobubble containing liquid flowing through it to electro-magnetic radiation. In one embodiment, the RDU 200 may be an ultraviolet (UV) disinfection unit, within which an ultraviolet light-emitting lamp 210 may be mounted or otherwise positioned. The lamp 210 may be conventionally powered, as by a ballast connected to AC power and to the lamp. Watertight and airtight conductor connections through enclosure 220 would typically be employed.

A power source, for example, batteries, solar cells, or other energy source may also be used to operate the unit 200. The lamp 210 may be enclosed in a protective quartz sleeve or any other material that is transparent to UV radiation, while protecting the lamp 210 from the liquid being circulated through the unit 200. In another embodiment, the lamp may also be immersed directly in the liquid being circulated through the RDU without the need for a protective UV transparent sleeve. In compartment 220, the liquid treated with the nanobubble generator 100a is forced to move in enclosure 220 through an inlet 222 and move towards outlet 224 while being exposed to ultraviolet light emanating from lamp 210. This exposes any microorganisms and pathogens that may have survived to that point to what are intended to be lethal levels of ultraviolet radiation.

Polar and non-polar liquid, hydrophilic and lipophilic liquid solutions may be used as a source liquid treated to create nanobubbles in the source liquid to produce treated solution having a high concentration of nanobubbles. As such, the source may include oils, alcohols, water, solvents, fuels, surfactants, gels, carbohydrates, oxidants, reductants, enzymes, fertilizers, micronutrients, nucleotides and so forth.

The system, method and apparatus may include a source liquid pre-treatment system (chemical treatment section), an optional high zeta potential crystal generator, an optional pre-filtration system, other optional filtration device (s), optional additional nanobubble generators or RDUs. Elements such as the pre-treatment system, nanobubble generators, RDU, zeta potential shift crystal generator, pre-filtration system, filtration device, are in liquid communication with one another and may be connected by way of a conduit system. The conduit system may include, for example, pipes, hoses, tubes, channels, and the like. In some cases, valves may be included to ensure that the flow of liquid is in the appropriate direction and, in some cases, unidirectional.

The source liquid solution, such as water (including wastewater, recycled water or tap water), oils, alcohols and the like, is supplied from a source (for example a faucet). The liquid may be stored in a reservoir, and may be supplied continuously or intermittently from the source to the system. The composition of source liquid may be tested and, if necessary, additional minerals and other constituents may be added at the chemical treatment section to provide a source liquid having the appropriate chemical content for disinfection. The source liquid may also be treated, prior or subsequent to holding in reservoir, in the pre-treatment system to substantially remove unwanted contaminants that may interfere with the subsequent treatment process(es), such as organic compounds, inorganic compounds, debris, oil-containing constituents, and the like.

In some embodiments, the system may include a method of injecting a suitable disinfecting chemical, such as chlorine dioxide (ClO2), into the source liquid (where needed). The method may include: mixing a first precursor with nanobubble-containing water to produce a first precursor solution, mixing a second chlorine dioxide precursor with nanobubble-containing water to produce a second precursor solution, and mixing the first and second precursor solutions in a reactor, thereby making chlorine dioxide containing source liquid. As noted above, in one example, the first precursor may be sodium chlorite (NaClO2) and the second precursor may be hydrochloric acid (HCl). More particularly, a first precursor solution may be about 7.5% NaClO2 in nanobubble-containing water, and a second precursor solution may be about 10% HCl in nanobubble-containing water.

Source liquid may be added continuously or intermittently to liquid reservoir. The liquid may flow through the nanobubble generator with enough force and pressure to initiate an endothermic reaction to create nanobubbles with paramagnetic attributes. A pump may be used to generate the force and pressure. As such, the liquid solution may be actively pumped at one or more points within the system or apparatus. The liquid may also be released using a gravity fed system or a passive system, such as located in a plume to treat the water before a water turbine or propeller.

In some embodiments, a filtration device may be provided to reduce or eliminate at least some bacteria, viruses, cysts, inorganic compounds, organic compounds, hormones, pharmaceutical compounds, endocrine chemicals and the like. Various filtration devices known in the art may be used. The filtration device may include, for example, particle filters, charcoal filters, reverse osmosis filters, active carbon filters, ceramic carbon filters, distiller filters, ionized filters, ion exchange filters, ultraviolet filters, back flush filters, magnetic filters, energetic filters, vortex filters, chemical oxidation filters, chemical addictive filters, Pi water filters, resin filters, membrane disc filters, microfiltration membrane filters, ultrafiltration membranes, nanofiltration membranes, cellulose nitrate membrane filters, screen filters, sieve filters, microporous filters, or the like and combinations thereof. The treated and filtered liquid may be stored or distributed for use and consumption.

High zeta potential crystal generators are known in the art and generally useful for prevention or reduction of scaling. One known high zeta potential crystal generator is the Zeta Rod™ system. The Zeta Rod™ system increases zeta potential of crystals by electronically dispersing bacteria and mineral colloids in liquid systems, eliminating the threat of bio-fouling and scale and significantly reducing use of chemical additives. Colloids in liquid systems become components of the capacitor and receive a strong boost to their natural surface charge, altering double-layer conditions that govern particle interactions. Mineral scale formation is intended to be prevented as the Zeta Rod™ system stabilizes the dispersion of colloidal materials and suspended solids, preventing nucleation and attachment of scale to wetted surfaces. Bacteria remain dispersed in the bulk fluid rather than attaching to surfaces, and cannot absorb nutrition or replicate to form slime and create foul odors. Existing biofilm hydrates excessively, loses bonding strength and disperses. Also, biological fouling, microbial induced corrosion, and scale formation are arrested by the Zeta Rod™ system.

The pre-filtration system is intended to reduce or substantially remove minerals, such as iron, sulphur, manganese, and the like from the treated source liquid. Pre-filtration system can be, for example, a stainless steel mesh filter. The treated and pre-filtered source liquid may be passed through the optional filtration device, wherein bacteria, viruses, cysts, and the like are substantially removed from the treated liquid. Preferably, microorganisms may be filtered from the liquid flow after being treated by radiation.

A pump may be provided, for example, downstream from the first nanobubble generator, such that treated liquid is released and distributed intermittently or continuously for various liquid system applications. The pump may alternatively be provided upstream from the first nanobubble generator.

The resulting disinfected or sanitized liquid, now having a high concentration of nanobubbles and treated by disinfecting chemicals and radiation, may be distributed to and stored in a storage container or it may be distributed for consumption or any appropriate uses.

Figure 6:
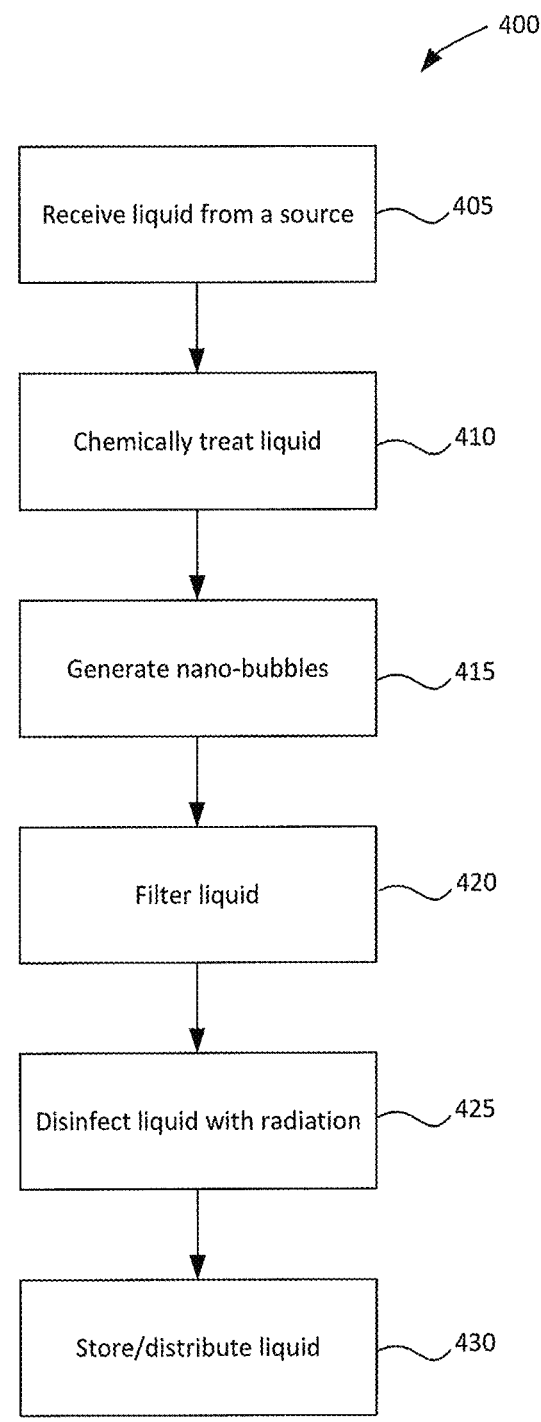
FIG. 6 is a flow chart of a method for liquid treatment.

FIG. 6 illustrates a method 400 for liquid treatment. At 405, liquid is received from a source. The liquid may be received by the system intermittently or continuously. As one simple example, water may enter the system from a standard well header.

At 410, the liquid receives a chemical test/treatment to test and, where necessary, adjust the chemical makeup of the liquid. In some cases, chemicals may be added to the liquid to produce a chemically treated liquid, as described herein. It will be understood that the source liquid may have already had some chemical treatment, such as the example where tap/city water is used as the source liquid. In this case, the chemical test may be conducted and treatment may be provided to adjust the chemical make-up of the source liquid. In some cases, the chemical make-up of the source liquid may be well understood and testing or treatment may not be necessary. In this type of situation, if no additional treatment is needed, the chemically treated source liquid may be directed via conduits past the chemical test/treatment unit (sometimes called pre-treatment unit). In some embodiments, the source liquid may receive a chlorine treatment, such as treatment with $ClO_2$ to become $ClO_2$-water. In some cases, $ClO_2$ may be injected at an appropriate level for disinfection, for example, 0.5 to 5 ppm. In some other cases, the level of $ClO_2$ may be 3 to 4 ppm.

At 415, nanobubbles are generated in the chemically treated liquid via a nanobubble generator. It is intended that the liquid will be passed through the nanobubble generator with enough force and pressure to initiate an endothermic reaction to create nanobubbles with paramagnetic attributes. As noted herein, in some embodiments, a pump may be used to generate the force and pressure.

At 420, the liquid may optionally be filtered. Filtration devices as detailed herein may be used to further treat the liquid. The method and system provided herein are intended to provide some advantages such as no fouling, no channeling, lower backwash flow, less waste process and handle, longer media life, lower headloss and a smaller footprint over standard water treatment media filtration systems. In some cases, the filters may include 40 micron safety filters that are intended to be easily inspected and serviced. The filters are intended to remain bio-foulant free which is intended to increase the filter's service life.

At 425, the chemically treated nanobubble liquid is disinfected by disinfecting radiation, for example, by receiving UV exposure. The UV exposure is intended to be coordinated with the nanobubble generators as disclosed herein and may be integrated with the nanobubble generator. In the case of UV radiation, the UV radiation may be provided at an appropriate level for disinfection (typically in a range of 40-50 mJ (millijoules) per $cm^2$ and, in some cases, may be applied at a higher level than would be typical because of the protective effect of the nanobubble generator on the chemical treatment versus the radiation treatment. In some cases, the UV radiation may be applied as a high dosage, for example 200 to 250 mJ (millijoules) per $cm^2$. It is intended that the UV exposure strongly reduces or annihilates organics, pyrogens and endotoxins.

At 430, the disinfected liquid flows out of the system and may be stored or distributed for use.

The system, method and apparatus described herein are intend to provide for less off gassing, greater ORP, greater efficacy for sanitizing and has been shown to be effective across a wide range of pH.

The combination of chemical treatment with nanobubble generation and RDU treatment is intended to provide improved disinfecting results. In particular, improved disinfecting results with a lower level of chemical treatment.

In particular, the nanobubble generator may change important properties such as oxidation-reduction potential (ORP) in chemically treated liquid. By increasing the ORP beyond the capability of existing chemical concentrations, the method is intended to enhance the efficacy of sanitizers. The nanobubble generator may increase ORP in excess of about 650 mV, which is intended to be enough to kill planktonic organisms instantaneously. The system and method may deliver ORP greater than 700 mV with relatively small amounts of sodium hypochlorite compared to conventional levels of sodium hypochlorite used (see Tables 1 and 2).

TABLE 1

Effect of 20 ppm of Sodium Hypochlorite/city water against several bacteria

| Culture | Sanitizer PPM | Orginal Count (cfu/ml) | Count after 15 minutes (cft/ml) |
|---|---|---|---|
| Psuedomonas sp. | 20 | 12,000 | <1 |
| Enterococcus sp. | 20 | 17,000 | <1 |
| Salmonella sp. | 20 | 11,000 | <1 |

TABLE 2

Effect of 5 ppm of Sodium Hypochlorite/Nanobubble-containing water against several bacteria

| Culture | Sanitizer PPM | Orginal Count (cfu/ml) | Count after 15 minutes (cft/ml) |
|---|---|---|---|
| Psuedomonas sp. | 5 | 12,000 | <1 |
| Enterococcus sp. | 5 | 17,000 | <1 |
| Salmonella sp. | 5 | 11,000 | <1 |

Research has shown that, at an ORP value of 650-700 mV, free-floating decay and spoilage bacteria as well as pathogenic bacteria such as *E. coli* 0157:H7 or Salmonella species are generally killed within 30 seconds. Spoilage yeast and the more-sensitive types of spore-forming fungi are also killed at this level after a contact time of a few minutes or less.

The WHO (World Health Organization) adopted an ORP standard for drinking water disinfection of 650 mV. When the ORP in a body of water measures 650 to 1000 mV, the sanitizer in the water is active enough to destroy harmful organisms quite quickly and some almost instantly.

Nanobubbles may condition surfaces via a nano-gaseous barrier. This nanogaseous barrier may serve to deter biofilm attachment to surfaces. The combination of the effects above creates a sanitized surface/system.

The method may also positively impact pH and increase the solubility effects of water. Only water pressure may be needed for operation.

Nanobubbles may ablate or distort surfaces intentionally placed in close contact with the nanobubbles as the nanobubbles collapse and cavitation occurs. In some contexts, cavitation is considered destructive and to be avoided, however, nanobubble formation and collapse may be used to promote and/or apply a protective finish to a surface.

Potable Water Systems

Embodiments of the system and apparatus herein may be integrated with various potable water systems. It has been discovered that water that has been chemically treated and then passed through a system incorporating a nanobubble generator and radiation-based disinfection unit can significantly reduce or eliminate bacteria and microorganisms in, and enhance quality of, all types of waters including potable, wastewater and recycled water, thereby preventing the formation of biofilm in various piping systems, as well as improving the taste of water. Potable water systems may include, but are not limited to, wells, springs, ponds, lakes, rivers, ocean sources with pretreatment and the like. Because of the generated nanobubbles in the water there may be more available oxygen for aerobic bacteria. Aerobic bacteria count increases, while anaerobic population decreases.

Food Processing Industry

It has been unexpectedly discovered that water treated by embodiments herein can act as a disinfectant with the addition of a minimal amount of chlorine (under 5 ppm) for storage of fresh produce. Since the treated water has been discovered to eliminate biofilm formation, food sanitation and production costs are lower and shelf life is extended. Further, since lower water surface tension increases solvency of the treated water, water treated in a system incorporating nanobubble generator and RDU has been found to generate this effect, greatly increases the yield of oils from teas and coffees.

Sanitation Applications The system can be integrated with sanitation systems such as swimming pools, power washers, car washes, household washing machines, commercial laundry facilities, household and commercial dishwashing facilities, industrial and food sanitation processes and the like.

Water Treatment Applications

The system can be integrated with water treatment applications such as water softeners, ion exchangers, all membrane and filter systems that utilize chlorine, chlorine dioxide, hydrogen peroxide, ozone, PAA and the like.

Chemical Treatment Applications

In some applications, a chemical treatment may be provided to alter a characteristic of the liquid rather than for sterilization. For example, in some liquid products, chemical treatment may be made to add color. If the liquid needs to be treated by UV to disinfect/sanitize, then the chemical treatment may be impacted by the UV radiation. The system herein provides some protection to the chemical treatment by the nanobubbles.

Figure 7A:
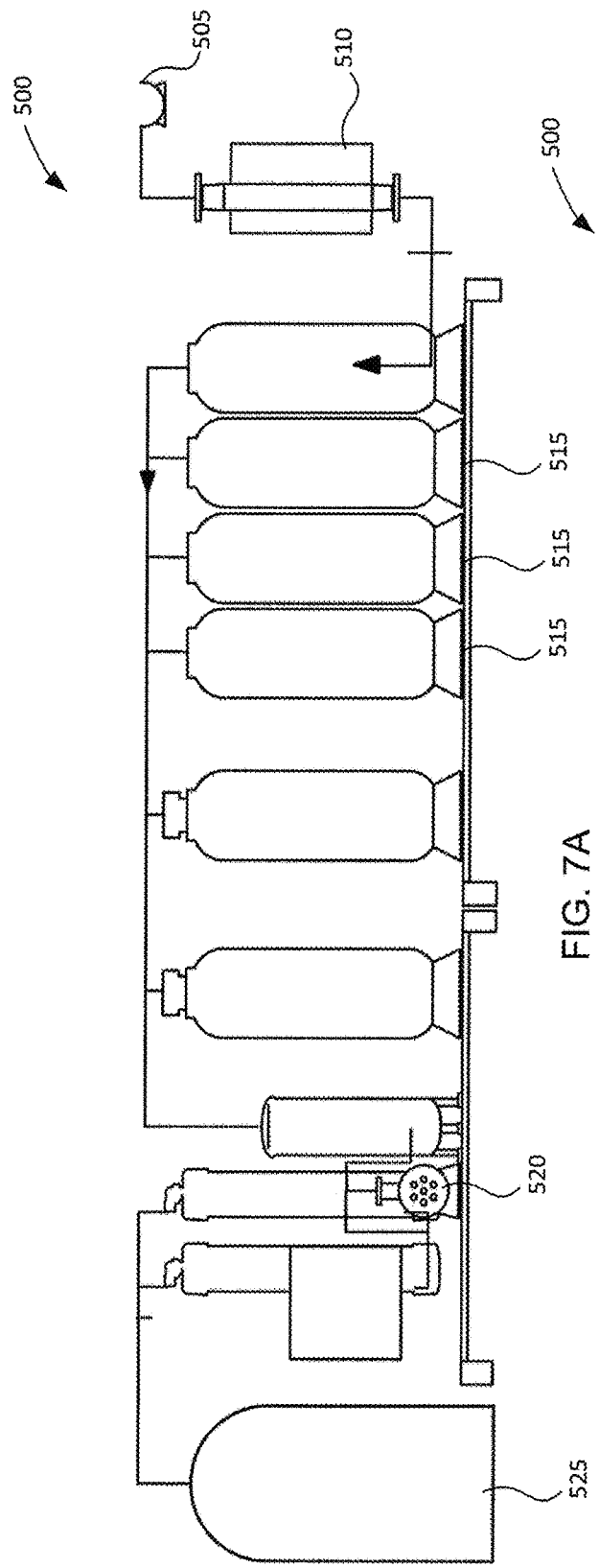
FIG. 7A illustrates a side view of a water treatment system according to an embodiment.
Figure 7B:
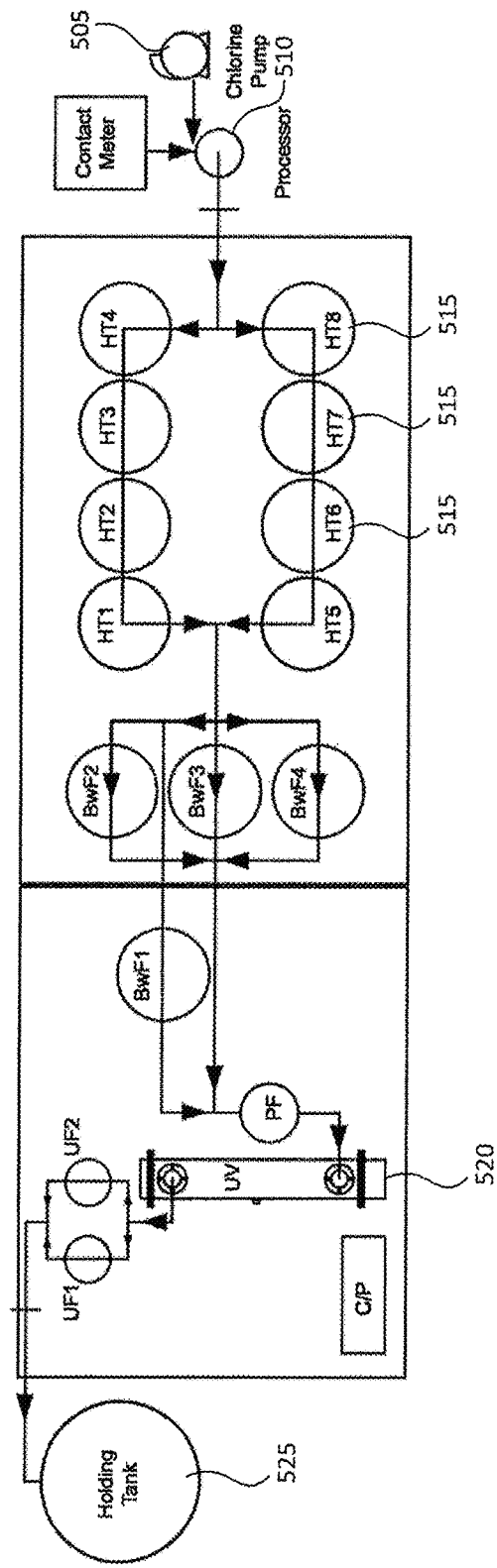
FIG. 7B illustrates a side view of the water treatment system of FIG. 7A.

In a specific example, and with reference to FIGS. 7A and 7B, a water treatment system 500 is illustrated. The treatment begins at a liquid source, such as a holding tank, cistern, or the like, possibly including city water that has been delivered. Where necessary, chemicals such as chlorine dioxide, which may be chlorine dioxide produced as described herein, is injected into the source water.

Chlorine dioxide may be injected into the water from a chlorine pump 505 and the water then passes through the nanobubble generator 510 where nanobubbles are introduced into the chlorinated water.

The $ClO_2$, nanobubble containing water then enters contact tanks 515 where iron, manganese, sulphur, and other toxic minerals are oxidized. Greensand plus media filters may be used to remove iron, manganese, radon, arsenic, sulfur compounds and so forth. Hydrocarbon filters may be used to remove or reduce oils, glyphosates and organophosphates.

The filtered water is then passed through a UV radiation unit 520 to further disinfect and, ideally, kill any remaining microorganisms.

A final filtration may then be performed using, for example, a Hydranautics HYDROcap® 60 ultra filtration membrane, to remove endotoxins, viruses, bacteria, both dead and live. The disinfected water may then be sent to a holding tank 525 or used.

Figure 8:
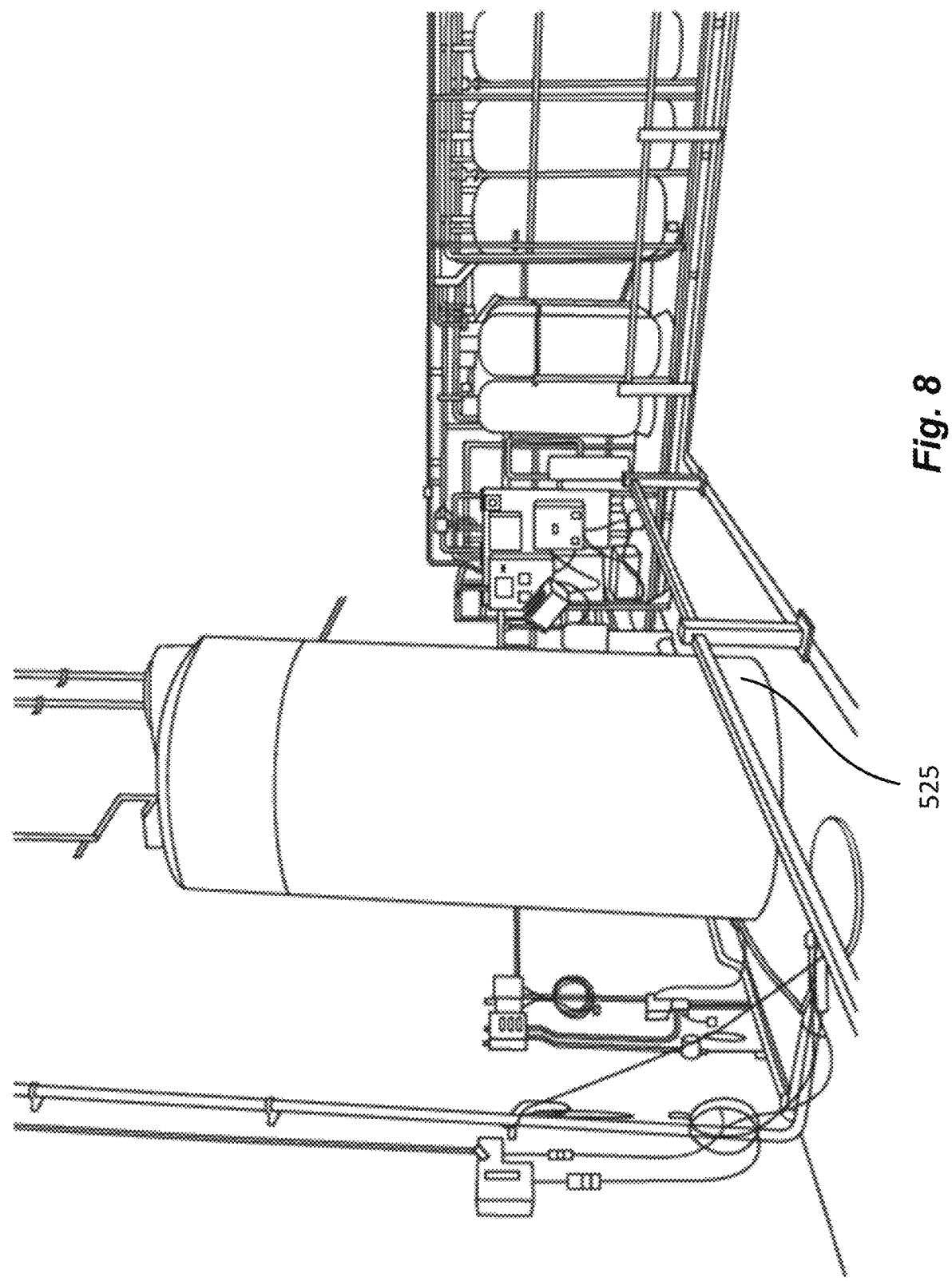
FIG. 8 is a photograph of a holding tank containing water treated with the system of FIG. 7A.

FIG. 8 is a photograph of a holding tank of water treated with a system such as that illustrated in FIG. 7A.

Although it may not be appreciated in the black and white photograph of FIG. 8, the water produced is blue in color (in this photo, the water is inside a white plastic water tank). The tank of FIG. 8 is 17 mm thick and the blue color is still readily apparent. It is believed that the chlorine, chlorine dioxide or any other chemical that is a gas in the water, is encapsulated in the nanobubbles created by the nanobubble generator. Therefore the color of the light reflected is the colour of the encapsulated gas, in this case chlorine. Interestingly, the chlorine gas inside the nanobubble still disinfects and measures an ORP. However, because the nanobubble that contains the gas reflects light, the gas is shielded from UV light or other light that may otherwise substantially photodegrade the gas in situ.

Through testing, there has been no evidence of any significant reduction in free or total chlorine or ORP from UV exposure even with chlorine dosages as low as 0.5 ppm. The same was observed with chlorine dioxide. A review of technical literature in the case of chlorine dioxide specifically would suggest that chlorine dioxide is very susceptible to UV degradation and should be kept in a dark location once generated. By encapsulating the chlorine dioxide in a nanobubble as described herein, a substantial portion of the chlorine dioxide dosed into a liquid stream can be protected from photolytic degradation.

Another feature of the method and system may be the prevention of off-gassing of chlorine dioxide solutions. From an environmental and health and safety perspective, workers in contact with chlorine dioxide solutions must be vigilant in how chlorine dioxide is applied to prevent off-gassing and worker exposure. From testing, it has been shown that the system and method may reduce the off-gassing potential by at least 50%.

There may also be the advantage that the system and method may slow the evaporation process so that pools, cooling towers, condensers and water features and the like experience less water loss and therefore require less makeup water.

In one experiment, untreated water was directed through a nanobubble generator. The nanobubble-containing water was used as feed water for a 2 Precursor Component Chlorine Dioxide Generator (DUPONT® OXYCHLOR® AC) using 10% HOCL (Hydrochloric Acid) and 7.5% NaClO2 (Sodium Chlorite) to form a batch solution of 800 PPM $ClO_2$ (Chlorine Dioxide). In some cases, the ppm of the batch solution may be increased by using more concentrated precursor chemicals. In this experiment, 3000 ppm $ClO_2$ was obtained.

This outcome was unexpected as it was noticed that there was a significant increase in ORP due to the nanobubbles and the chlorine dioxide did not gas off, even at 9 ppm strength. It is noted that $ClO_2$ usually measures in the 550 to the 600 mV range of ORP.

It was also noted that a 95% and 100% conversion of the sodium chlorite into chlorine dioxide was obtained. The usual conversion of a 2 component generator is between 60% and 70% with a high level of residual NaClO2. This calculation was done by calculating the amount of chemical used and consumption over a two day period.

No off gassing has been observed at levels above 0.3 PPM. It was noted that no off gas was noted at any rate similar to 9 ppm.

In a second experiment, 800 ppm of chlorine dioxide was injected into source water. The chlorine dioxide containing water was processed through a nanobubble generator. The output from the nanobubble generator was held in contact tanks for an average contact time of 30 minutes. The chlorine dioxide in the contact tank was measured at 3.6 ppm. From the contact tank, the chlorine dioxide containing water was passed through KATALOX LIGHT® Media Filters. The water came out at 3.1 ppm of $ClO_2$. The $ClO_2$ treated water then went through 20 micron cartridge filters and through 200 mJ (millijoules) of ultra violet (UV) radiation using a system similar to that of FIG. 1. After UV treatment, the $ClO_2$ in the water was reduced by only 0.4 ppm to 2.7 ppm. At a level of 200 mJ, it would have been expected that most or all of the $ClO_2$ in the water would have been removed. From the UV treatment, the $ClO_2$-water was run through Hydranautics HYDRAcap® 60 ultrafiltration membranes rated to 80 KDaltons. At the end of the process the chlorine dioxide was measured around 2.5 ppm. However the ORP was in excess of 760 millivolts, which was an unexpected result.

The $ClO_2$-water was provided to cows. Within four days the farm's ammonia and methane emissions had been significantly reduced by greater than 70% and at the furthest point of the farm in the drinking water trough it was noted that a chlorine dioxide residual of 0.3 ppm with no biofilm was observable. Over time the average chlorine dioxide level at the drinking water troughs is expected to increase to 1 ppm. The chlorine dioxide demand for good oxidation of manganese, iron and other metals is around 3.6 to 3.8 ppm.

In some cases, where the system is in service, the system is making water at 3.1 ppm $ClO_2$ at the multi-media filter (MMF) Inlet, 2.7 ppm at MMF Outlet, 2.5 ppm at UV Outlet, 2.4 ppm at UF discharge, 1.9 ppm at Clearwell Overflow and 0.17 ppm at drinkers (i.e. animal watering stations).

The system and method described herein are intended to have lowered zeta potential for colloidal coagulation and flocculation, higher ORP for control of biologicals, higher surface area for quicker reactions rates and no or reduced bio or chemical fouling potential.

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether elements of the embodiments described herein are implemented as a software routine, hardware circuit, firmware, or a combination thereof.

Embodiments of the disclosure or components thereof can be provided as or represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor or controller to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor, controller or other suitable processing device, and can interface with circuitry to perform the described tasks.

The above-described embodiments are intended to be examples only. Alterations, modifications and variations can be effected to the particular embodiments by those of skill in the art without departing from the scope, which is defined solely by the claims appended hereto.

The invention claimed is:

1. A liquid treatment system comprising:
   a source of liquid to provide a source liquid;
   a chemical treatment station to chemically test the chemical content of the source liquid and provide an appropriate amount of chemical treatment to the source liquid to provide a chemically treated liquid;
   a nanobubble generator in fluid communication with the chemical treatment station that generates nanobubbles in the chemically treated liquid to provide a nanobubble liquid;
   a radiation-based disinfecting unit (RDU) in fluid communication with the nanobubble generator that exposes the nanobubble liquid to radiation and provides a nanobubble treated liquid;
   a pump to produce a liquid flow through the system; and
   an outlet through which the treated liquid flows.

2. The liquid treatment system of claim 1, wherein the nanobubble generator includes a housing having an inflow portion for receiving a source liquid, an outflow portion for releasing a nanobubble containing liquid, and a treatment portion disposed between the inflow and outflow portions for treating the source liquid, the treatment portion having at least two sequential shear surface planes separated by cavitation spaces, chambers or zones.

3. The liquid treatment system of claim 1, wherein the RDU comprises:
   an RDU inlet operatively connected to the nanobubble generator;
   a disinfecting unit in fluid communication with the RDU inlet comprising an enclosure and a radiation emitting means; and
   a RDU outlet for releasing a radiation-treated liquid from the disinfecting unit.

4. The liquid treatment system of claim 3, wherein the radiation is ultra-violet radiation.

5. The liquid treatment system of claim 1, wherein the testing the chemical content comprises determining if the source liquid contains an appropriate amount of chemical for disinfecting the source liquid in conjunction with the nanobubble generator and the RDU.

6. The liquid treatment system of claim 5, wherein the chemical comprises chlorine dioxide.

7. The liquid treatment system of claim 6, wherein the chlorine dioxide is injected to provide between approximately 0.5 and 5 ppm at the nanobubble generator.

8. The liquid treatment system of claim 7, wherein the chlorine dioxide is injected to provide between approximately 3 and 4 ppm at the nanobubble generator.

9. The liquid treatment system of claim 1, wherein the pump produces a pressure at the nanobubble generator of between approximately 1 and approximately 10 bar.

10. A method of treating a liquid, the method comprising passing a source liquid through a liquid treatment system of claim 1.

11. The system of claim 1, wherein the source liquid is water, including potable, wastewater and recycled water.

12. A method of treating a liquid, the method comprising:
   receiving a source liquid;
   chemically testing the source liquid and, providing an appropriate amount of chemical treatment to the source liquid to provide a chemically treated liquid;
   passing the chemically treated liquid through a nanobubble generator to produce a nanobubble-containing liquid at a pressure of between approximately 1 bar and approximately 10 bar;
   treating the nanobubble-containing liquid with disinfecting radiation to produce a resultant liquid; and
   releasing the resultant liquid for use.

13. The method of claim 12, wherein the chemically treated liquid comprises a source liquid exposed to chemical treatment to produce the chemically treated liquid.

14. The method of claim 13, wherein the chemical treatment comprises injecting a suitable amount of chemical into the source liquid.

15. The method of claim 14, wherein the suitable amount comprises an amount of chemical for disinfecting the source liquid in conjunction with the nanobubble generator and the disinfecting radiation.

16. The method of claim 12, wherein the flow of liquid is driven at a pressure of between approximately 1 bar and approximately 10 bar at the nanobubble generator.

17. The method of claim 12, wherein the radiation is ultra-violet radiation.

18. The method of claim 17, wherein the ultra-violet radiation is delivered at approximately 250 mJ/cm$^2$.

* * * * *